(12) United States Patent
Jörgensen

(10) Patent No.: US 7,022,106 B2
(45) Date of Patent: Apr. 4, 2006

(54) CATHETER HAVING ENHANCED DISTAL PUSHABILITY

(75) Inventor: Ib Erling Jörgensen, Haigerloch (DE)

(73) Assignee: Abbott Laboratories Vascular Entities Limited, Galway (IE)

(*) Notice: Subject to any disclaimer, the term of this patent is extended or adjusted under 35 U.S.C. 154(b) by 0 days.

(21) Appl. No.: 11/199,780

(22) Filed: Aug. 9, 2005

(65) Prior Publication Data

US 2005/0273052 A1    Dec. 8, 2005

Related U.S. Application Data

(62) Division of application No. 09/999,493, filed on Nov. 30, 2001, now Pat. No. 6,960,188.

(51) Int. Cl.
*A61M 29/00* (2006.01)

(52) U.S. Cl. .............. 604/103.09; 604/96.01; 606/192

(58) Field of Classification Search ........ 604/103.09, 604/96.01, 523–526, 102.02; 606/194, 195, 606/191, 192
See application file for complete search history.

(56) References Cited

U.S. PATENT DOCUMENTS

| | | | |
|---|---|---|---|
| 4,024,873 A | 5/1977 | Antoshkiw et al. | |
| 4,646,742 A | 3/1987 | Packard et al. | |
| 4,665,925 A | 5/1987 | Millar | |
| 4,702,252 A | 10/1987 | Brooks et al. | |
| 4,892,519 A | 1/1990 | Soner et al. | |
| 4,955,895 A | 9/1990 | Sugiyama et al. | |
| 5,085,636 A | 2/1992 | Burns | |
| 5,176,637 A | 1/1993 | Sagae | |
| 5,378,238 A | 1/1995 | Peters et al. | |
| 5,403,339 A | 4/1995 | Nobuyoshi et al. | |
| 5,425,712 A | 6/1995 | Goodin | |
| 5,503,631 A | 4/1996 | Onishi et al. | |
| 5,626,600 A | 5/1997 | Horzewski et al. | |
| 5,755,707 A | 5/1998 | Miyagawa et al. | |
| 5,759,191 A | 6/1998 | Barbere | |
| 5,827,242 A | 10/1998 | Follmer et al. | |
| 5,830,227 A | 11/1998 | Fischell et al. | |
| 6,027,475 A | 2/2000 | Sirhan et al. | |
| 6,066,157 A | 5/2000 | Barbere | |
| 6,152,912 A | 11/2000 | Jansen et al. | |
| 6,186,978 B1 | 2/2001 | Samson et al. | |

FOREIGN PATENT DOCUMENTS

| GB | 1566674 | 5/1980 |
|---|---|---|
| WO | WO9515192 | 6/1995 |

*Primary Examiner*—Nicholas D. Lucchesi
*Assistant Examiner*—Matthew DeSanto
(74) *Attorney, Agent, or Firm*—Nicola A. Pisano, Esq.; Luce, Forward, Hamilton, Scripps LLP

(57) ABSTRACT

Apparatus for enhancing pushability and minimizing kinking of a balloon catheter is provided, wherein a catheter comprises inner and outer tubes, and a balloon that is proximally affixed to the outer tube and distally affixed to the inner tube. The outer tube extends distal to the proximal affixation point and at least partially into the balloon segment to provide additional stiffness and pushability. The outer tube may taper and connect to the inner tube or to radiopaque markers disposed thereon. The outer tube further may be selectively reinforced, as by using multipart construction or using different tube textures, to selectively provide added stiffness in areas susceptible to kinking.

16 Claims, 3 Drawing Sheets

CATHETER HAVING ENHANCED DISTAL PUSHABILITY

CROSS-REFERENCE TO RELATED APPLICATIONS

This application is a divisional of application Ser. No. 09/999,493 filed Nov. 30, 2001, now U.S. Pat. No. 6,960,188.

FIELD OF THE INVENTION

The present invention relates to a surgical catheter, and more particularly, a balloon catheter having a reinforced distal segment to facilitate catheter pushability and minimize kinking.

BACKGROUND OF THE INVENTION

Angioplasty and stenting are widely used techniques for treating vascular disease. In balloon angioplasty, a catheter having an inflatable balloon affixed to its distal end is guided through a patient=s vasculature with the balloon in a deflated state, and the balloon is positioned within a vascular lesion. The balloon then is inflated to compress the atherosclerotic plaque against the vessel wall to restore adequate blood flow in the vessel. Stenting involves the deployment of small tubular prostheses, either balloon expanded or self-expanding, that radially expand to maintain vessel patency, and are commonly used in conjunction with balloon angioplasty.

One problem associated with the use of balloon catheters is that kinks may develop along the catheter. Because the catheter must be relatively flexible to be advanced through tortuous vasculature, a flexible catheter is prone to kink when pushed from its proximal end by the physician. This is especially so when the distal end encounters resistance from a tight stenosis. The term "pushability" describes the ability of a catheter to transmit longitudinal forces from the proximal to the distal end, without creating kinks, and this is an integral characteristic of a successful catheter design.

Previously-known balloon catheters have attempted to enhance pushability primarily by reinforcing a proximal segment of the catheter. U.S. Pat. No. 5,626,600 to Horzewski et al. (Horzewski) describes a balloon dilatation catheter comprising proximal and distal extremities, an inflation lumen extending therethrough, a balloon disposed on the distal extremity that communicates with the inflation lumen, and a separate guidewire lumen. A small plug may be disposed within the guidewire lumen to separate the guidewire lumen into a proximal stiffening section and distal guidewire section. A stiffening mandrel may be inserted into the proximal stiffening section of the guidewire lumen, proximal to the plug, to influence proximal stiffness and to enhance pushability of the catheter. According to the patent, the apparatus strives to enhance catheter pushability by proving a catheter having a stiff proximal portion, a soft distal portion and a very soft low profile tip portion.

One drawback associated with the catheter described in the Horzewski patent is the potential for kinks to develop at the distal end of the catheter, i.e., near the balloon. The stiff proximal section may be readily advanced, but the location where the soft distal portion joins the stiff proximal section may be particularly susceptible to kinking. This adverse event is especially likely to occur when the very soft distal section is attempted to be pushed through a tight stenosis because there is no distal reinforcement.

Furthermore, the distal end of the above-described balloon catheter would be particularly susceptible to kink when used during a stenting procedure. This is because mounting a stent over the balloon increases the rigidity of the soft distal section, and the joint between the soft and rigid segments is susceptible to kink when the catheter is pushed forcefully.

Other catheter designs have provided an outer tube that extends through the balloon segment to the distalmost end of the catheter. U.S. Pat. No. 5,085,636 to Burns (Burns) describes a catheter comprising an elongated flexible tube having an inflatable balloon at its distal end. There is one single lumen for both the guidewire and inflation/deflation functions, as a pair of distal valves provide a fluid tight seal around the guidewire during inflation and deflation of the balloon. The patent suggests that the elongated flexible tube that extends to the distalmost end of the catheter may be of an integral or multipart construction.

The Burns patent specifically recommends manufacturing the proximal section from "hypotube" (stainless steel hypodermic needle tube), while the distal segment comprises a flexible polymer tube. Like the Horzewski device, Burns strives to increase overall pushability by providing a primarily reinforced proximal segment. However, like the device described in the Horzewski patent, the flexible distal end of the device in the Burns patent still will be susceptible to kinking, when it encounters a tight stenosis. In particular, kinking may occur at the proximal balloon connection because at this location a flexible polymer tube section is disposed between the stiff hypotube section and the relatively stiff balloon section.

In view of these drawbacks of previously known balloon catheters, it would be desirable to provide apparatus that increases the push force transmitted from the outer tube to the distal end of the catheter, e.g., to facilitate pushability of the distal end through a tight stenosis.

It still further would be desirable to provide apparatus having a substantially continuous stiffness transition between the outer tube of a coaxial catheter and the stent section of the catheter.

It still further would be desirable to provide apparatus that minimizes the formation of kinks near the distal end of a balloon catheter.

SUMMARY OF THE INVENTION

In view of the foregoing, it is an object of the present invention to provide apparatus that increases the push force transmitted from the outer tube to the distal end of the catheter, e.g., to facilitate pushability of the distal end through a tight stenosis.

It is another object of the present invention to provide apparatus having a substantially continuous stiffness transition between the outer tube of a coaxial catheter and the balloon section of the catheter.

It is another object of the present invention to provide apparatus that minimizes the formation of kinks near the distal end of a balloon catheter.

These and other objects of the present invention are accomplished by providing apparatus suitable for enhancing distal pushability of a balloon catheter. The apparatus preferably comprises a catheter having an outer tube, an inner guidewire tube that extends coaxially within the outer tube, and a balloon disposed near the distal end of the catheter. The balloon is affixed at a proximal affixation point to the outer tube, and affixed at a distal affixation point to the inner tube. Unlike previously-known catheter designs, the outer tube extends at least partially through the balloon segment, i.e., distal to the proximal balloon affixation point, and the outer tube may be reinforced to increase stiffness and pushability along this segment of the catheter.

In a preferred embodiment, the outer tube gradually tapers just distal to the proximal affixation point. The taper extends at least partially through the balloon segment to a smaller diameter, such that it does not substantially increase the overall distal profile of the catheter. An inflation aperture is provided in the outer tube at a location just distal to the proximal affixation point.

The apparatus further preferably comprises at least one radiopaque marker affixed to the inner tube and disposed within the balloon segment. The distal end of the outer tube may be affixed to the radiopaque marker to enhance stiffness within the balloon segment and increase pushability of the catheter through a tight stenosis. Alternatively, the outer tube may taper distal to the proximal balloon affixation point and connect directly to the inner tube, such that the outer tube and inner tube become a single reinforced tube.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
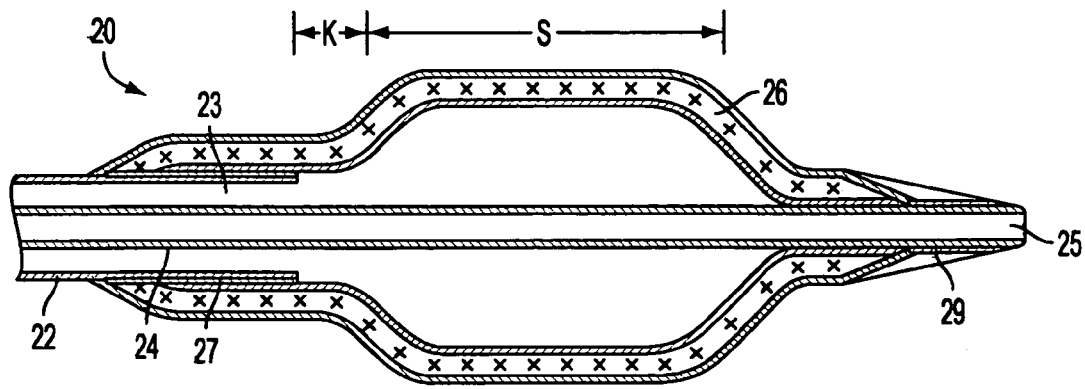
FIG. 1 is an illustration of the distal end of a previously-known coaxial catheter design.

Referring to FIG. 1, a previously-known balloon catheter from U.S. Pat. No. 5,492,532 to Ryan et al. (Ryan) is described. Catheter 20 comprises outer tube 22, inner tube 24, and balloon 26 having proximal and distal ends, the proximal end of balloon 26 being affixed to outer tube 22 at proximal affixation point 27 and distally affixed to inner tube 24 at point 29. Outer tube 22 and inner tube 24 are provided in a coaxial alignment, such that inflation lumen 23 communicates with balloon 26 while guidewire lumen 25 allows catheter 20 to be advanced over a guidewire.

One drawback associated with this previously-known design is that outer tube 22 terminates at proximal affixation point 27. Consequently, the segment distal to outer tube 22 will be susceptible to kinking when the distal end of catheter 20 is advanced into a tight stenosis. The push force provided at the proximal end of catheter 20 may not be fully transmitted to the distalmost end of catheter 20, in part because outer tube 22 terminates at point 27.

The previously-known catheter design in FIG. 1 further is susceptible to kinking when used in a stenting procedure. For example, if a stent is mounted on balloon 26, it may span section S and form a relatively rigid segment along this portion of catheter 20. Because outer tube 22 also provides a relatively rigid segment, the flexible segment K may be formed between outer tube 22 and proximal end of stent section S will be susceptible to kinking when the distal end of catheter 20 encounters a tight stenosis.

Figure 2A:
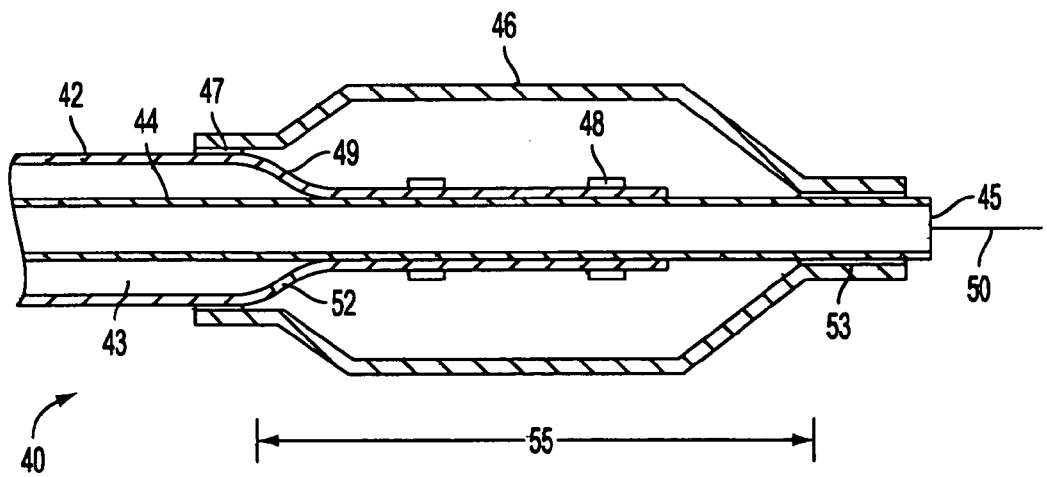
FIGS. 2A–2C are a schematic of the distal end of a reinforced catheter in accordance with the present invention, and a helical stiffening coil having constant and varying pitches, respectively.

Referring to FIG. 2A, catheter 40 constructed in accordance with principles of the present invention is described. Catheter 40 comprises proximal and distal ends, of which the distal end is depicted in FIG. 2. The proximal end of catheter 40 communicates with a traditional proximal hub assembly (not shown) that comprises a proximal guidewire entry port and an inflation/deflation port.

The distal end of catheter 40 comprises outer tube 42, inner tube 44 and balloon 46, each having proximal and distal ends. Inner tube 44 extends coaxially within outer tube 42 and extends beyond the distal end of balloon 46. Inflation/deflation lumen 43 and guidewire lumen 45 communicate with the proximal inflation/deflation port and guidewire entry port, respectively. Guidewire lumen 45 of inner tube 44 is configured to permit the advancement of catheter 40 over guidewire 50.

The proximal end of balloon 46 is affixed to outer tube 42 at proximal affixation point 47, e.g., using a solder, weld or biocompatible adhesive, while the distal end of balloon 46 is affixed to inner tube 44 at distal affixation point 53, as shown in FIG. 2A. The area extending between proximal and distal affixation points 47 and 53 defines balloon segment 55. The apparatus preferably further comprises radiopaque markers 48 affixed to inner tube 44 and disposed within balloon segment 55.

In accordance with principles of the present invention, outer tube 42 extends distally beyond proximal affixation point 47 to enhance stiffness within balloon segment 55. Outer tube 42 preferably comprises taper 49 that reduces the diameter of outer tube 42 within balloon segment 55 to reduce the overall distal profile. Alternatively, taper 49 may be omitted and tube 42 may continue at its original diameter throughout balloon segment 55.

In a preferred embodiment, outer tube 42 tapers inward just distal to proximal affixation point 47, and the distal end of outer tube 42 is affixed to one or more radiopaque marker bands 48, as shown in FIG. 2A. The reduced diameter distal section of tube 42 may extend the entire length of balloon segment 55 and may be affixed to inner tube 44 and the distal end of balloon 46 at distal affixation point 53.

In the embodiment described in FIG. 2A, outer tube 42 comprises at least one inflation aperture 52 disposed in a lateral surface at a location distal to point 47 and proximal to the most proximal radiopaque marker 48. Inflation aperture 52 permits fluid communication between the proximal inflation/deflation port and balloon 46 via lumen 43. In an alternative embodiment, outer tube 42 may terminate proximal to the most proximal radiopaque marker within balloon segment 55, in which case the distalmost tip of tube 42 would communicate directly with balloon 48 via lumen 43.

Figure 2B:
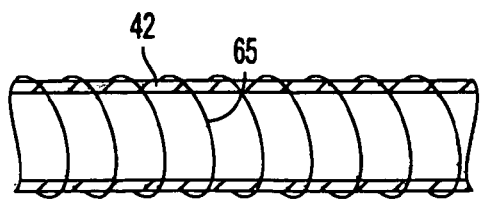
Figure 2C:
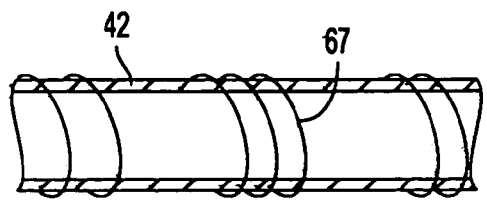

The characteristics of outer tube 42 may vary along its length to influence stiffness at selected locations, particularly to provide increased stiffness along balloon segment 55. The characteristics of outer tube 42 may be varied regionally by providing a rigid section, braided or spiral-shaped section, or by providing bores or slits at selected locations. FIGS. 2B and 2C illustrate embodiments wherein helical coils 65 and 67, having constant and varying pitches, respectively, may be used to selectively enhance stiffness of outer tube 42. Helical coils 65 and 67 may enhance stiffness of outer tube 42 proximal to or within balloon segment 55. Optionally, outer tube 42 may be affixed to inner tube 44 at selected locations along catheter 40, e.g., using a solder or weld, to enhance stiffness and pushability so long as inflation lumen 43 is not completely blocked.

Outer tube 42 may be manufactured using a single-wall tubing, or may be provided as co-extruded tubing to allow for different surface properties inside and outside the tubing. The characteristics of catheter 40 further may be altered by manufacturing outer tube 42 using at least one material along its length, e.g., a combination of stainless steel and polymeric materials using adhesives or advanced extrusion techniques. It should be appreciated that providing different materials and/or varying the textures of outer sheath 42 at any combination of locations is intended to fall within the scope of the present invention.

Figure 3A:
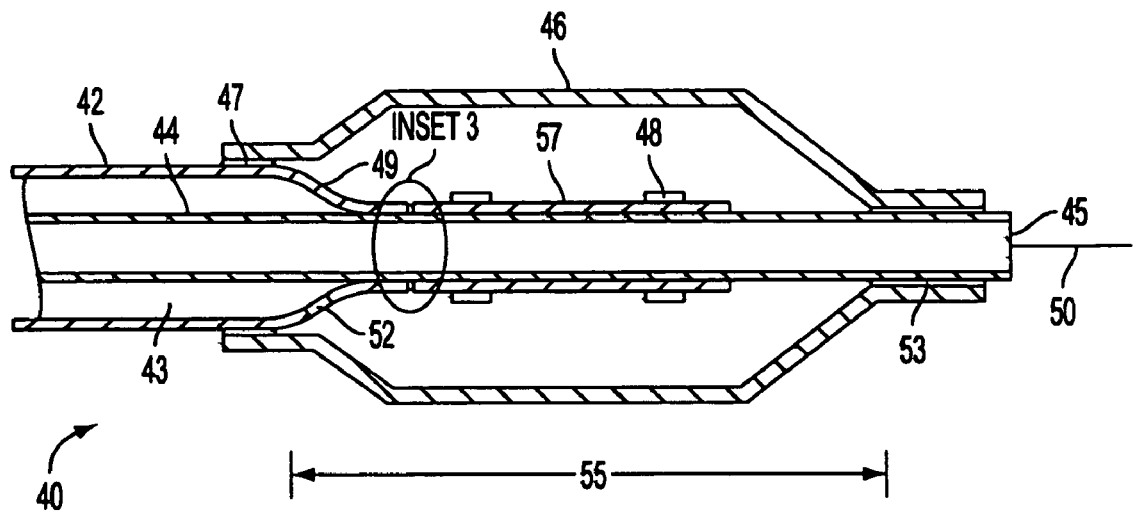
FIGS. 3A–3C describe an alternative embodiment of the present invention having a separate connecting tube, and means for affixing the connecting tube to the outer tube using a butt-weld and lap-weld, respectively.
Figure 3B:
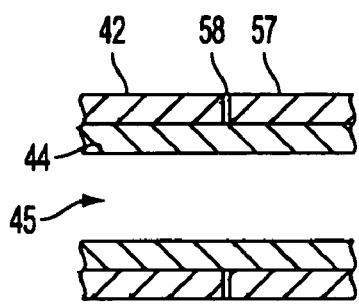
Figure 3C:
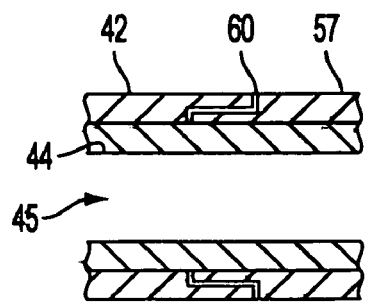

Referring to FIG. 3, an alternative embodiment of catheter 40 is described wherein the distal end of outer tube 42 communicates with a separate connecting tube 57 having proximal and distal ends. Connecting tube 57 is disposed within balloon segment 55 and preferably is affixed to at least one radiopaque marker 48, as shown. The distal end of outer tube 42 may be affixed to the proximal end of connecting tube 57, e.g., using biocompatible adhesive. FIGS. 3B–3C, corresponding to inset 3 of FIG. 3A, illustrate outer tube 42 being affixed to connecting tube 57 via butt-weld 58 and lap-weld 60, respectively. Lap-weld 60 is preferred to butt-weld 58 because lap-weld 60 may be less susceptible to kink as push forces are transmitted from outer tube 42 to connecting tube 57. The embodiments described in FIGS. 3 provide reinforced tube segments of differing characteristics without having to manufacture one relatively complicated piece for outer tube 42. Furthermore, connecting tube 57 prevents kinks from developing between radiopaque markers 48, an otherwise common location for the formation of kinks.

Figure 4:
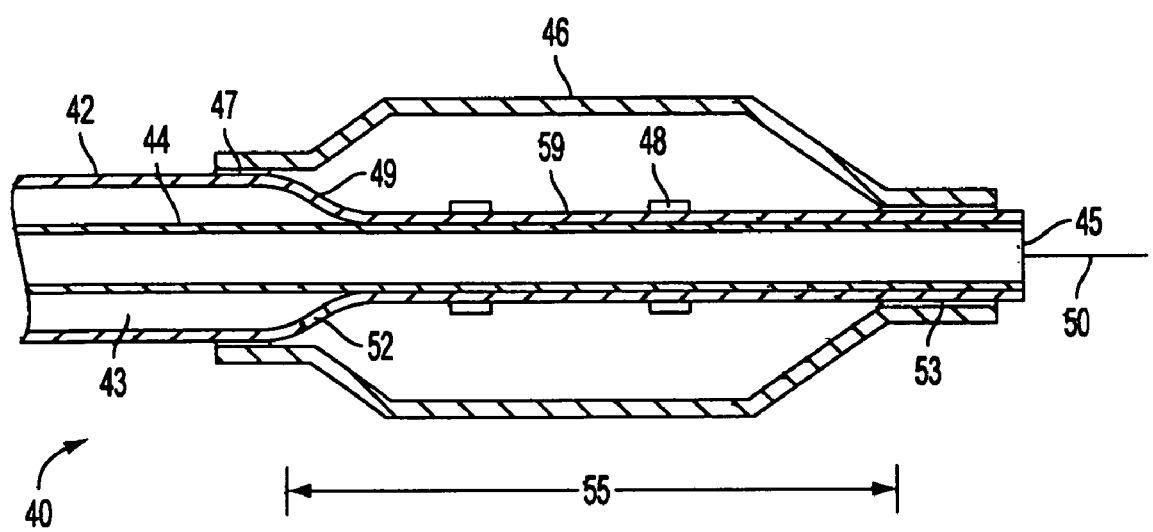
FIG. 4 describes an alternative embodiment of the present invention having an outer tube that tapers to connect to the inner guidewire tube.

Referring to FIG. 4, an alternative embodiment of catheter 40 in accordance with the present invention is described. Outer tube 42 is affixed to the proximal end of balloon 46 at proximal affixation point 47, then tapers via taper 49 to connect to inner tube 44. In this embodiment, outer tube 42 and inner tube 44 become a single, reinforced tube 59 when connected. As described hereinabove, the properties of outer tube 42 and reinforced tube 59 may be tailored to provide varying stiffness at selected locations along the length of catheter 40.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. Apparatus suitable for enhancing pushability of a balloon catheter, the apparatus comprising:
   an outer tube having proximal and distal ends;
   a connecting tube having proximal and distal ends;
   an inner tube having proximal and distal ends and a guidewire lumen extending therethrough, the inner tube disposed coaxially within the outer tube to define an inflation lumen therebetween; and
   a balloon having proximal and distal ends, wherein the proximal end of the balloon is affixed to the outer tube at a proximal affixation point and the distal end of the balloon is affixed to the inner tube at a distal affixation point to define a balloon segment extending therebetween,
   wherein the outer tube tapers just distal to the proximal affixation point to a reduced diameter segment, the connecting tube is coupled to the reduced diameter segment and has an outside diameter equal to that of the reduced diameter segment, and the reduced diameter segment and connecting tube are affixed to the inner tube and the connecting tube extends at least one-half of the length of the balloon segment to increase pushability of the balloon, but does not extend to the distal affixation point, a tapered portion of the outer tube just distal of the proximal affixation point defining an inflation aperture proximal of the distal end of the outer tube.

2. The apparatus of claim 1 wherein the outer tube compromises a plurality of different materials at selected locations along its length to selectively influence stiffness.

3. The apparatus of claim 2 wherein the outer tube compromises a polymeric material.

4. The apparatus of claim 3 wherein the outer tube compromises stainless steel.

5. The apparatus of claim 1 wherein the distal end of the outer tube is affixed to the proximal end of the connecting tube.

6. The apparatus of claim 5 wherein the outer tube is affixed to the connecting tube using a biocompatible adhesive.

7. The apparatus of claim 1 wherein sections of the outer tube include a helical coil that enhances stiffness of the outer tube.

8. The apparatus of claim 7 wherein a pitch of the helical coil varies along a length of the outer tube.

9. The apparatus of claim 1 wherein the reduced diameter segment further comprises a butt-weld between the outer tube and the connecting tube.

10. The apparatus of claim 1 wherein the reduced diameter segment further comprises a lap-weld between the outer tube and the connecting tube.

11. The apparatus of claim 1 further comprising at least one inflation window disposed in a lateral surface of the outer tube at a location distal to the proximal affixation point.

12. The apparatus of claim 1 further comprising at least one radiopaque marker affixed to the connecting tube.

13. The apparatus of the claim 1 wherein the reduced diameter segment, connecting tube and the inner tube form a single reinforced tube.

14. The apparatus of claim 1 wherein sections of the outer tube include braiding that vary the stiffness of the outer tube.

15. The apparatus of claim 1 wherein the outer tube is manufactured using a single-wall material.

16. The apparatus of claim 1 wherein the outer tube is provided as co-extruded tubing having different properties on inner and outer sides of the tubing.

* * * * *